United States Patent [19]

Rhenter et al.

[11] Patent Number: 4,693,724

[45] Date of Patent: Sep. 15, 1987

[54] TOTAL HIP PROSTHESIS WITH PRIMARY FIXATION

[76] Inventors: Jean L. Rhenter, 57 rue Michelet, 42000 Saint Etienne; Jean Collomb, L'Olagnier, 26800 Portes les Valence, both of France

[21] Appl. No.: 820,636

[22] Filed: Jan. 21, 1986

[30] Foreign Application Priority Data

Jan. 31, 1985 [FR] France .................................. 85 01528

[51] Int. Cl.$^4$ ............................................... A61F 2/32
[52] U.S. Cl. .................................................... 623/23
[58] Field of Search ........................ 623/16, 17, 18, 19, 623/20, 21, 22, 23; 128/926, 926 A

[56] References Cited

FOREIGN PATENT DOCUMENTS

| | | | |
|---|---|---|---|
| 0019042 | 11/1980 | European Pat. Off. | 623/23 |
| 2607315 | 9/1976 | Fed. Rep. of Germany . | |
| 2839093 | 3/1980 | Fed. Rep. of Germany | 623/23 |
| 2242065 | 3/1975 | France . | |
| 2295729 | 7/1976 | France . | |
| 2350824 | 12/1977 | France . | |
| 2024631 | 1/1980 | United Kingdom | 623/23 |

Primary Examiner—Richard J. Apley
Assistant Examiner—David Isabella
Attorney, Agent, or Firm—Parkhurst & Oliff

[57] ABSTRACT

Total hip prosthesis with primary fixation is provided with three essential parts:

a femoral pin, for insertion into the femur;
a cotyloidal cupule, for engagement into the acetabulum of the treated hip; and
a prosthetic neck, covered with a sphere which joins the pin to the cupule and is intended to make the articulation proper. The threaded femoral pin has a special tulip-shaped anatomical profile, with a progressively variable radius.

6 Claims, 6 Drawing Figures

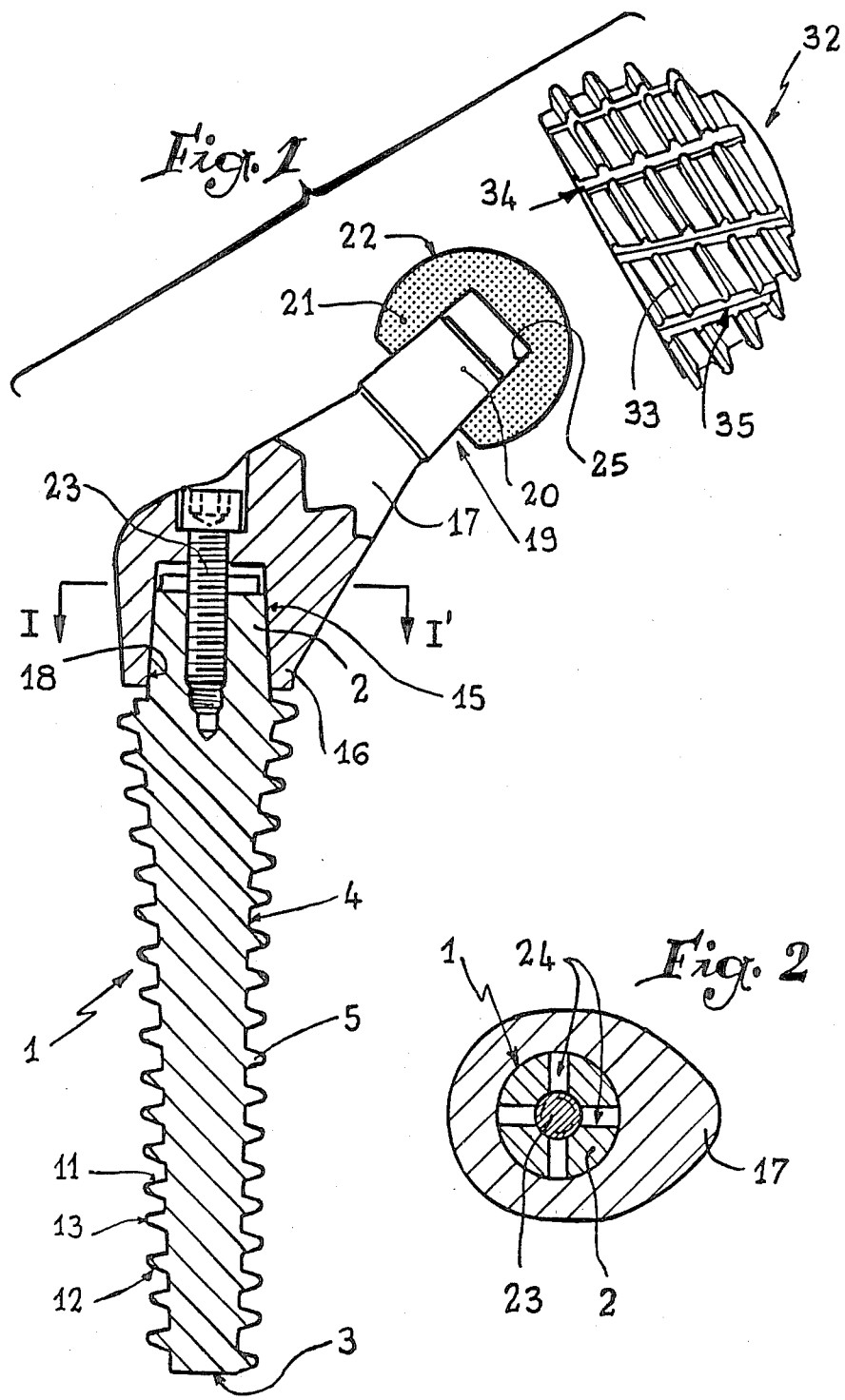

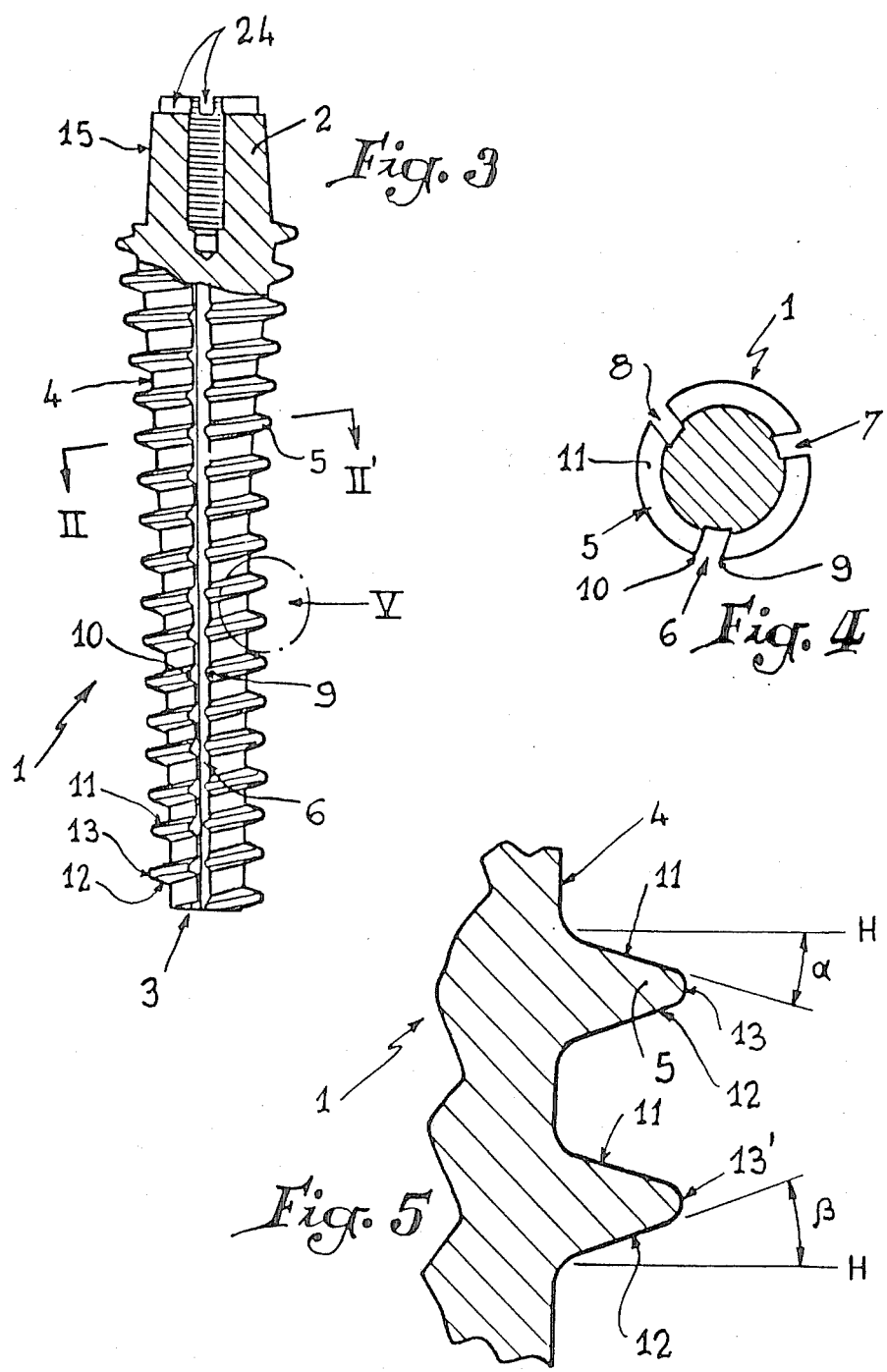

TOTAL HIP PROSTHESIS WITH PRIMARY FIXATION

BACKGROUND AND SUMMARY OF THE INVENTION

The present invention relates to a new total hip prosthesis with primary fixation.

As conventionally known, there are essentially two categories of hip prosthesis.

In the first category, the prosthesis is cemented. But this solution presents two types of problems:

problems during surgery due to anaesthetic shocks caused by the cement itself; and problems after surgery, namely risks of infection where the bone joins up with the cement, loosenings and difficulties in re-operating, if the prosthesis needs to be changed eventually, because the bone, which has been drilled in, has become brittle.

The second category, which is now progressively spreading, is called "prosthesis with primary fixation". In this type of prosthesis, the pin is force-fitted into the bone by adjustment and the bone re-formation occurs according to a special design of that pin. This type of prosthesis is essentially constituted by three principal parts, namely, in the right order:

a femoral pin, for insertion into the femur;

a cotyloidal cupule, for engagement into the acetabulum of the treated hip;

a prosthetic neck, covered with a sphere, which joins the pin to the cupule and is intended to make the articulation proper.

Numerous solutions have heretofore been proposed to produce such prostheses.

For example, it has been suggested to screw the femoral pin into the femur and, like a screw, to give to said pin a slightly truncated shape so as to make the screwing operation easier (as described for example, in European Pat. No. 0010527 and in French Pat. No. 2 295 729). Such conicity however, is often ill-adapted to the shape of the femur, this causing an inaccurate adjustment, hence a wrong distribution of the stresses. Moreover, the threads used up to now, have been found to create risks of unscrewing, either due to the insufficient length of the thread or due to the drawing-back effect on the supporting flange. This causes postoperative pains possibly due to stress peaks occuring at the level of this thread.

European Pat. No. 000549 and French Pat. No. 2 481 596 both propose to provide on the head of the pin which is not engaged into the femur, a co-axial flange, of which the lower face rests against the femur, whereas the upper face is provided with position locating and holding means, this permitting the location and holding of the angular position of the prosthetic neck with respect to the pin during assembly. Although this solution offers a great number of advantages, in practice, as the flange rests on the reduction, this causes an important resection of the bone and can give rise to fractures on the upper end of the femur, and particularly in the zone known as the "trochanter". Moreover, from the very structure of this flange, it is impossible to obtain an ideal orientation of every case of anteversion of the femoral prosthetic neck.

It is the object of the present invention to overcome the above disadvantages by proposing a total hip prosthesis with primary fixation which eliminates all of the aforesaid problems, namely a total hip prosthesis with primary fixation which:

is better adapted to the shape of the femur, hence which can be better adjusted;

reduces the stress peaks on the level of the thread;

improves the primary fixation and reduces resection of the upper end of the femur;

and finally, which permits an ideal orientation of the anteversion of the prosthetic neck.

The total hip prosthesis with primary fixation according to the invention, is of the type formed of three principal parts:

a threaded femoral pin, designed to be screwed into the femur, a cotyloidal cupule, designed to be engaged in the cotyloidal cavity of the treated hip; and a prosthetic neck, topped by a sphere joining the head of the pin to the cupule and designed to ensure the articulation proper, said prosthesis being characterized in that the threaded femoral pin has a tulip-shaped tapered longitudinal section, widening from the bottom end towards the head with progressively variable radius.

In other words, the invention relates to a total hip prosthesis with primary fixation, wherein the threaded femoral pin has a special tulip-shaped anatomical profile, with progressively variable radius.

By "profile with progressively variable radius" is meant a longitudinal profile of which the radius of curvature varies permanently and progressively from the point of the pin, where it reaches its maximum, to its head, hence a profile of which the radius of the section increases progressively from the point to the head.

Advantageously, in practice:

the section of the pin is circular;

the thread of the threaded femoral pin, as well as that of the cupule, have a bevelled trapezoidal section with advantageously rounded angles.

In said trapezoidal thread, the upper face is less inclined with respect to the direction of the thread than the lower face with respect to the same plane of the pin cross-section;

the angle of inclination of the upper face with respect to the plane of said cross-section is between 15° and 25°, and preferably around 20°, and the angle of inclination of the upper face with respect to that same plane, is between 10° and 20°, and preferably around 15°;

the threaded pin is also provided with longitudinal slots situated according to generatrices, the angles of incidence of which are inclined particularly in both directions, in order to help the screwing and unscrewing operation;

the fitting of the prosthetic neck over the threaded head and over the sphere-shaped prosthetic articulation head is achieved by means of two conical bores of low-inclination, respectively male and female bores.

BRIEF DESCRIPTION OF THE DRAWINGS

The invention will be more readily understood on reading the following description with reference to the accompanying drawings, in which:

FIG. 1 is a cross-sectional view of a total prosthesis with primary fixation according to the invention.

FIG. 2 illustrates a cross-section along axis I—I' of FIG. 1.

FIG. 3 is a detailed view of the threaded pin according to FIG. 1.

FIG. 4 is a cross-sectional view through axis II—II' of FIG. 3.

FIG. 5 is an enlarged view of the threading according to the invention and more precisely of the encircled part referenced V in FIG. 3.

DETAILED DESCRIPTION OF THE PREFERRED EMBODIMENT

Figure 6:
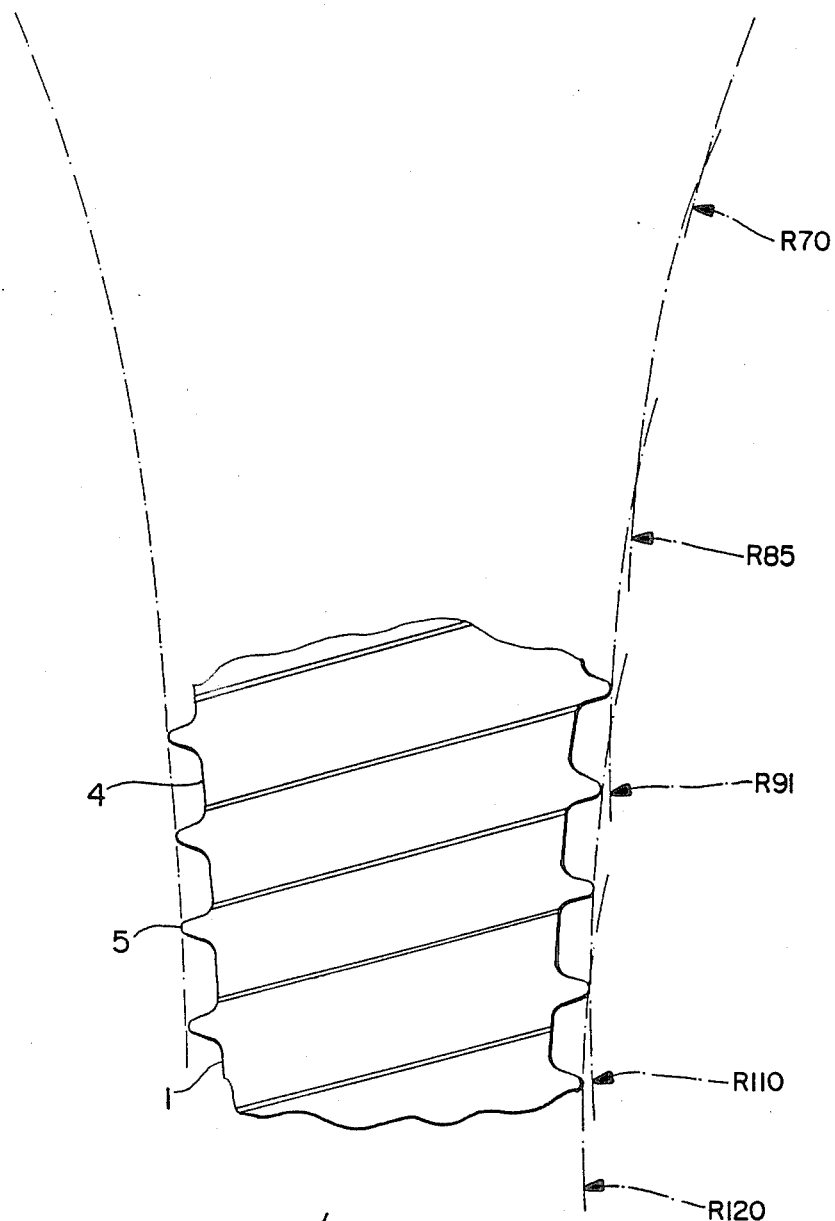
FIG. 6 illustrates the stem profile with progressively variable radius.

Referring now to the figures, the total prosthesis according to the invention is composed first of a threaded femoral pin of circular cross-section (1), of which the head (2) is wider than the point (3) and which, according to the invention, has a tulip-shaped longitudinal section (4) of progressively variable radius, widening from the point (3) up towards the head (2). This particular anatomical flared profile has a curvature which varies permanently and progressively and continues, hence of variable radius, of which the profile resembles a three-degree polynomial. By way of indication, according to one advantageous embodiment, the diameter of the pin (1) at the point (3) is 18 mm (the thread included) and at the opposite end towards the head (2), 30 mm, whereas in its middle part it is only 20.5 mm for a total thread length of 95 mm.

Said pin (1) may be made of any conventional material such as for example stainless steel, metal alloy, ceramic. Advantageously, said pin is in titanium and preferably, the outer surface of said pin is coated with a fine layer of ceramic, and in particular aluminium oxide.

Said pin (1) is provided with a thread (5) of which the pitch has a bevelled trapezoidal cross-section with rounded angles, as illustrated in detail in FIGS. 3 and 5.

Said pin (1) is also provided on its generatrices with three longitudinal slots (6,7 and 8) respectively, angularly offset by 120°, the angles of incidence (9) and (10) of which are inclined particularly in both directions to allow screwing and unscrewing. In practice, such angles of incidence have sharp angles. Thus, said three slots (6,7,8) forming open notches, help the screwing action and if necessary the unscrewing by self-tapping, hence advantageously permitting a reduction of the quantity of ancillary material.

According to another embodiment of the invention (see FIGS. 3 and 5), the thread (5) of the pin (1) has a bevelled trapezoidal cross-section with rounded edges. In said thread (5), the upper face (11) of the trapeze with respect to the direction of the threading, namely the screwing direction, is less inclined than the lower face (12) of said trapeze. Angle α formed between the upper face (11) and the horizontal H is between 10° and 20°, and preferably around 15° in order to be part of the angle of incidence and to ensure a good hold of the pin (1) inside the femur. Angle β formed between said horizontal H and the lower face (12) is between 15° and 25°, and preferably around 20°, in order to provide an efficient angle of incidence. As illustrated in FIG. 5, the angles (13,13' between the bevels (11,12) are rounded.

Unexpectedly, the tulip-shaped characteristic profile with progressively variable radius illustrated in FIG. 6 can adapt nearly perfectly to the shape of the corticals of the upper end of the femur. Consequently, said profile enables an excellent adjustment of the pin and improves the distribution of the strains between the prosthesis and the bone.

Likewise, unexpectedly, the already known trapezoidal thread presents, when applied to the hip prosthesis, specific advantages, as, not only does it improve the extracting strength, it also improves the distribution of the stresses, and in doing so it reduces the stress peaks.

The head (2) proper of the pin (1) ends into a conical bearing surface (15) of which the top angle is around 6°. Said male conical bearing surface (15) fits over the corresponding female part of the base (16) of the prosthetic neck (17), and this inside a female cone (18) of corresponding shape.

Said prosthetic neck (17) produced from the same material as the pin (1), for example titanium, is then provided at its base (16) with a slightly conical female part (18), and at its head (19) with another upper conical bearing surface (20) designed to engage inside a corresponding conical female surface (25) of the spherical prosthetic head (21) proper. The angle of the engaging cone (19,20) is close in value to the angle of the engaging cone (15,18) is around 3° (Morse cone). Said engagement, which is already wellknown in the mechanical field, and has already been proposed in prostheses (see for example French Pat. No. 1 017 927 and European Pat. No. 0000549) is easy to produce. Moreover, it permits an ideal orientation of the anteversion of the femoral prosthetic neck (17).

Mounting of the prosthetic neck (17) on the pin (1) has been achieved by means of a setting screw (23).

The angle formed between the longitudinal axis of the prosthetic neck (17) and the longitudinal axis of the pin (1) is around 135°.

The spherical prosthetic head (21) then fits over the cotyloidal cupule which, in known manner, is designed to engage into the cotyloidal cavity of the treated lip.

Said cupule (see FIG. 1) is first composed of a conventional piece, now shown, in high density polyethylene, the hollow inner shape of which is designed to rest against the contacting part (22) of the head (21) and of which the external part embeds itself in the cupule proper (32) which latter thus forms a receptacle and has an ovoidal external shape. According to an advantageous embodiment, said contacting part (22) is constituted by a layer of titanium nitride deposited in gaseous phase, for example over a thickness of three to ten microns. The cupule (32), likewise in titanium, has an outer shape which substantially corresponds to that of the socket, this permitting an improvement of the transmission of the forces to the pelvis. Said cupule (32) is also provided with a trapezoidal threading (33) similar to thread (5) and also with a series of self-tapping longitudinal notches (34,35).

Advantageously, the trapezoidal threading (33) of the bevelled cupule (32) with rounded corners has the same characteristics as the thread (5) of the plate (1). Likewise, according to an advantageous embodiment of the invention, the thread of the plate (1) and that of the cupule (32) are composed of six ribs.

The prostheses according to the invention present many advantages over the commercial solutions used heretofore. Amongst these solutions, can be cited by way of example:

the reduction, if not complete disappearance of the stress peaks at the level of the thread, due quite unexpectedly, to the special design given to the thread pitch, namely bevelled trapezoidal profile with rounded angles; hence a considerable reduction of post-operative pains;

the slightly flared tulip-shape with progressively variable radius which is better adapted to the shape of the femur than the conical design, and as a result permits a better anatomical ajdustment;

the absence of flanges which reduces the importance of the bone resection of the upper end of the femur, thus reducing the risk of fracture of the trochanter;

finally due to the ready engagement by cone of low inclination which is a wellknown method in the mechanical field and for this type of application, an ideal orientation of the anteversion of the prosthetic neck for each case, which could never be obtained before now;

and the easy positioning with only a small amount of ancillary material due to the self-tapping nature of the plate.

What is claimed is:

1. An improved total hip prosthesis with primary fixation, comprising:
   a threaded femoral pin for threadable insertion into a medullary cavity of a femur, said pin having a head at a proximal end and a distal end at an opposite end from said head;
   a cotyloidal cupule for engagement with the acetabulum of a threaded hip; and
   a prosthetic neck, the neck having a sphere for joining the head of a pin to the cupule;
   the threaded femoral pin having a circular cross-section in a plane orthogonal to a sagital plane and along the entire length of the pin an anatomical profile in a sagital plane defined by a radius of curvature which continuously non-linearly varies from said distal end of said pin toward said head of said pin.

2. The total hip prosthesis of claim 1 wherein a thread on said femoral pin has a bevelled trapezoidal longitudinal cross-section with rounded edges, an upper inclination angle defined between an upper face of said trapezoidal cross-section and a horizontal plane is less than a lower inclination angle defined between the horizontal plane and a lower face of said trapezoidal cross-section.

3. The total hip prosthesis of claim 2 wherein said upper inclination angle is in a range of 15°–20°; and said lower inclination angle is in a range of 10°–20°.

4. The total hip prosthesis of claim 1, wherein the pin is provided on its generatrices with longitudinal slots.

5. The total hip prosthesis of claim 1 wherein one of the prosthesis neck and the head of the pin includes a tapered bore, and the other of said neck and said head includes a correspondingly tapered cone, said cone being received in said tapered bore for joining said neck and said pin.

6. The total hip prosthesis of claim 1 wherein said femoral pin, the prosthetic neck, the head of said pin and the cupule are made of titanium, and wherein a frictional surface of said sphere is coated with a layer of titanium nitride for cooperating with said cupule.

* * * * *